United States Patent [19]

Charney

[11] Patent Number: 4,879,233
[45] Date of Patent: Nov. 7, 1989

[54] NOVEL *ASPERGILLUS NIVEUS* MICROORGANISM USED FOR THE CHIRAL REDUCTION OF CARBONYL GROUPS

[75] Inventor: William Charney, Montclair, N.J.

[73] Assignee: Schering Corporation, Kenilworth, N.J.

[21] Appl. No.: 309,461

[22] Filed: Feb. 10, 1989

[51] Int. Cl.$^4$ .......................... C12N 1/16; C12R 1/66; C12P 7/02
[52] U.S. Cl. .................................. 435/254; 435/129; 435/156; 435/171; 435/913
[58] Field of Search ............... 435/254, 913, 129, 156, 435/914–920, 171

[56] References Cited

U.S. PATENT DOCUMENTS

| | | | |
|---|---|---|---|
| 3,860,488 | 1/1975 | Cooper | 435/913 |
| 3,880,895 | 4/1975 | Greenspan | 435/911 |
| 4,004,978 | 1/1977 | McMullen | 435/911 |
| 4,029,779 | 6/1977 | Petzoldt et al. | 435/911 |
| 4,054,595 | 10/1977 | Marx et al. | 435/911 |
| 4,153,509 | 5/1979 | Schwartz | 435/912 |
| 4,619,919 | 10/1986 | Gold et al. | 514/166 |
| 4,658,060 | 4/1987 | Gold et al. | 514/166 |

OTHER PUBLICATIONS

Derwent Abs., 81-09893D/07, Truckenbro et al., DD-144758 (11-1980).
Derwent Abs., 89-025482/04 Radunz et al., EP-300287 (1-1989).
Derwent Abs., 85-172993/29 Sehgal et al., EP-148612 (7-1985).
Chem. Abs. CA89-89474(11) Reddy et al. Indian J. Microbioc., vol 26 (3-4), pp. 178-181 (1986).
Chem. Abs. CA06-72276(10) Hiremath et al., Environ. Ecol., vol. 3 (1), pp. 568-571 (1985).
Chem. Abs. CA07-175176 (19) Tani Kagaku (KGZKA3) (109) pp. 191-205 (1986).
Chem. Abs. CA10-111464 (13) Yamazaki et al., Agric. Biol. Chem. (ABCHA6), vol. 52 (12), pp. 3239-3240 (1988).
Cem. Abs. CA01-189610 (21) Sih et al., Angew Chem. (ANCEAD), vol. 96 (8), pp. 556-565 (1984).
Chem. Abs., CA80-44531 (9) Kamal Sci. Cult., vol. 39 (7), pp. 320-323 (1973).
J. Am. Chem. Soc., (1980) 108, 162-169, Keinan et al.

*Primary Examiner*—Herbert J. Lilling
*Attorney, Agent, or Firm*—John J. Maitner; Stephen I. Miller; James R. Nelson

[57] ABSTRACT

There is disclosed a novel microorganism *Aspergillus niveus*, ATCC 20922, and a process for chiral reduction of ketones using said mircoorganisms.

1 Claim, No Drawings

NOVEL ASPERGILLUS NIVEUS MICROORGANISM USED FOR THE CHIRAL REDUCTION OF CARBONYL GROUPS

The present invention relates to microbiological chiral reduction of carbonyl groups and to a novel microorganism for carrying out this reduction. More particularly, the invention relates to the microbiological chiral reduction of ketone groups. The novel microorganism is *Aspergillus niveus* (ATCC 20922).

The invention also relates to a process for preparing the compound dilevalol using the novel microorganism.

The compound (-)-5- {(1R)-1-hydroxy-2-[(1R)-1-methyl-3-phenylpropyl)amino]ethyl} salicylamide monohydrochloride, Compound I, also known as dilevalol hydrochloride, exhibits potent vasodilating β-adrenergic blocking activity and is useful for the treatment of hypertension; see U.S. Pat. No. 4,619,919.

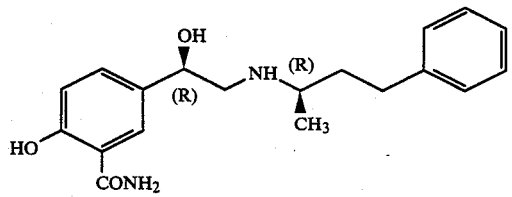

I

Stereospecific processes for preparing dilevalol are described in the above noted patent and in U.S. Pat. No. 4,658,060. In preparing dilevalol, chiral reduction of a ketone group is required to afford the proper R stereoisomer configuration. The inventor investigated more than 50 cultures of microorganisms reported to reduce ketone groups to hydroxy groups, for example, bacterial such as Schizomycetes; fungi, such as Ascomycetes, Basidiomycetes and Phycomycetes; however none of the microorganisms tested were active in reducing the ketone group to the proper R stereoisomer. The inventor then searched for new microorganisms from the soil and discovered a microorganism, *Aspergillus niveus* which was capable of reducing the ketone group to a hydroxy group having the proper R stereo configuration.

SUMMARY OF THE INVENTION

The present invention embraces the novel microorganism *Aspergillus niveus* (ATCC 20922) and mutants and variants thereof having the distinguishing characteristics of *Aspergillus niveus*.

The present invention is also directed to a process for chiral reduction of ketone groups to hydroxy groups, which comprises cultivating the microorganism *Aspergillus niveus* in a medium to which a ketone compound has been added so that a stereospecific hydroxy group can be formed and accumulated in said medium, and collecting said hydroxy compound. The process is particularly useful in preparing dilevalol from 5-{(R)-[(1-methyl-3-phenylpropyl)amino]acetyl} salicylamide.

DETAILED DESCRIPTION OF THE INVENTION

The microorganim *Aspergillus niveus* was discovered and isolated by the present inventor from soil obtained from an excavation site in Union, N.J., U.S.A. Separation of the microorganism was accomplished by the soil enrichment method, wherein a sample of soil is mixed with a compound which restricts the growth to those organisms that can use that compound. In this particular case, the compound 5-(methoxyacetyl)-2-hydroxybenzamide was added to the soil sample and the mixture was incubated for several days. From time to time the mixture was sampled using standard microbiological methods and plated out. A number of isolates were purified and tested. One of the isolates was very active in reducing the ketone group of the test substrate. This active pure culture, a white mold, was characterized as belonging to the genus Aspergillus and was further identified as *Aspergillus niveus*.

The bacteriological characteristics of *Aspergillus niveus* are as follows:

(a) Growth in various media:

(1) Malt extract agar medium:

It grows in abundance in this medium forming a white colony, raised and floccose in center, smooth, with condial heads not apparent to the unaided eye. Outer portion of colony flat, velvety, consisting of abundant conidial heads arising from hyphae appressed to the surface of the agar. Exudate lacking. Colony reverse yellow-brown. Conidial heads at first radiate, becoming loose columnar, sometimes flaring slightly at apex, white, Conidiophores erect, with a distinct foot cell, relatively thick-walled, sometimes with septa, occasionally branched. Conidiophores hyaline in optical view but with a distinct brownish tint in surface view. Apex of conidiophore enlarging gradually to form a vesicle. Vesicles hemisphaerical, bearing sporogenous apparatus on upper surface. Sporogenous apparatus biseriate, but occasionally uniseriate, especially in small heads or at margin of vesicle. Biseriate heads consisting of metulae, bearing phialides that taper to a slender tip. Phialides bearing long chains of conidia. Conidia globose, smooth, thin-walled, hyaline.

(2) Czapek agar medium:

It grows in abundance in this medium forming a colony heavily floccose, surface appearing smooth and compact with conidial heads not apparent to the unaided eye. Colony white, with a light yellowish-cream or buff color with age. Conidial heads formed amidst aerial mycelium of colony as described on malt extract agar, except slightly smaller and not as uniformly columnar.

(3) V-8 juice agar medium:

It grows in abundance in this medium forming a white colony, heavily floccose in center, moderately floccose in outer region; center of colony soon becoming light yellow, entire colony cream to yellow-buff with age. Conidial heads abundant, formed on aerial mycelium, as described on malt extract agar.

(b) Physiological Properties;

(1) Formation of aflatoxin: negative.

(c) Source: soil

A viable culture of *Aspergillus niveus* has been deposited in the collection of the American Type Culture Collection (ATCC) in Rockville, Md., where it has been assigned accession number ATCC 20922. Should the deposited culture become lost, destroyed on non-viable during the longer of the thirty (30) year period from the date the culture was deposited or the five (5)

year period after the last request for the deposited culture or the effective life of the patent which issues from this application, the culture will be replaced, upon notice, by applicants or assignee(s) of this application. Subcultures of *Aspergillus niveus*, ATCC 20922, are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the US Patent Laws.

The process aspect of the present invention provides a method for microbiological chiral reduction of ketone groups to the corresponding hydroxy group having the proper stereo configuration.

The microbiological chiral reduction process of the present invention is illustrated by the preparation of dilevalol from 5- {((R)-[(1-methyl-3-phenylpropyl)amino]acetyl} salicylamide:

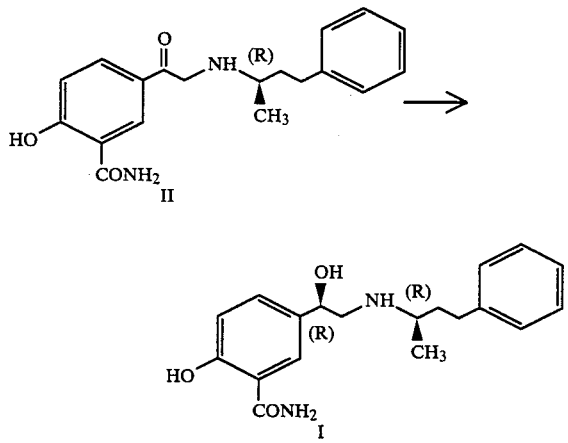

The microbiological chiral reduction is carried out by adding the ketone substrate, compound II, to the culture broth of the microorganism. The incubation may be conducted at temperatures in the range between 26° C. and 35° C., but preferably in the range between 33° C. and 34° C., while maintaining the pH value of the reaction mixture in the range between 6.5 and 7.2, but preferably between 6.8 and 7.2.

The concentration of the ketone substrate in the reaction mixture may vary from 10 to 50 mg/100 ml, and preferably 25 mg/100 ml.

The duration of the chiral reduction reaction may vary from 48 to 120 hours, preferably 72 hours.

At the end of the reduction reaction, there may be extracted from the reaction mixture dilevalol by using organic solvents, such as, for example, ethyl acetate, methylene chloride, and the like.

From the organic extract thus obtained and concentrated, there may then be separated dilevalol. Purification of the hydroxy compound may be carried out by TLC and HPLC chromatography.

Other known microorganisms of the genus Aspergillus have been investigated to determine whether other members of genus class would afford clincal reduction of keto groups. The following microorganisms failed to provide chiral reduction of ketone groups: *Aspergillus niger* (ATCC 1394); *Aspergillus Orxyae* (ATCC 1454); and *Aspergillus Oryzae* (ATCC 11488).

The present invention will be described in more detail by the following examples. However, these examples are not intended to limit the scope of the present invention.

EXAMPLE 1

The novel fungus *Aspergillus niveus* was isolated in pure culture by the "soil enhancement method". Master cultures of the active strain were prepared and maintained by the usual microbiological methods one or more of the following agar media: potato dextrose, Sabouraud's agar and yeast extract dextrose agar.

Inoculum for fermentation was prepared by subculture to the following sterile liquid medium:

| Ingredient | Amount |
| --- | --- |
| Soy flour | 35 g |
| Potato dextrin | 50 g |
| Cerelose | 5 g |
| Calcium carbonate | 5 g |
| Cobalt chloride 6H$_2$O | 2 mg |
| Soft water | to one liter |
| Post sterile pH | 7.0–7.2 |

The broth was dispensed into 300-ml flasks containing 100 ml of broth per flask.

The flasks were seeded either with spores or mycelium from agar slants and incubated in a water temperature controlled shaker operated at 320 strokes per minute at 32°–34° C. Excellent growth was achieved in 18–48 hours. At that time the bio-conversion production medium was inoculated at 2.5% level with seed from the above-noted medium. The production medium comprises per liter: 5.6 grams of autolyzed yeast; 10 grams cerelose and 2.5 grams mono-basic potassium phosphate. The broth (100 ml) was dispensed into 300 ml flasks and sterilized at 121° C. for 30 minutes; post sterile pH 5.0–5.2.

After inoculation, the flasks were placed in an incubator shaker running at 320 strokes per minute at 34° C. At the end of 24 hours, 50 mg of the hydrochloride salt of 5-{(R)-[(1-methyl-3-phenylpropyl)amino]acetyl} salicylamide either dry or dissolved in 1–2 ml of dimethylformamide was added to each flask and incubation continued on the shaker for 24–72 hours. Samples were taken periodically to determine the rate of conversion of the 5-{(R)-[(1-methyl-3-phenylpropyl)amino]acetyl} salicylamide to dilevalol.

Sample size was 10 ml placed into a 25×150 ml test tube. Ethylacetate (25 ml) was then added to each tube and shaken 50–60 times. The solvent layer was allowed to settle and then drawn off and evaporated on a steam bath to dryness. The residue was dissolved in 2 ml of methanol and subjected to TLC and HPLC chromatography. Thin layer chromatography indicated a bioconversion of 70–80% of the 5-{(R)-[(1-methyl-3-phenylpropyl)amino]acetyl} salicylamide to dilevalol.

I claim:

1. A biologically pure culture of the fungus *Aspergillus niveus*, ATCC 20922, said culture being capable of chiral reduction of ketones.

* * * * *